(12) United States Patent
Bae

(10) Patent No.: US 10,595,810 B2
(45) Date of Patent: Mar. 24, 2020

(54) MEDICAL IMAGING APPARATUS AND METHOD OF SCANNING THEREOF

(71) Applicant: SAMSUNG ELECTRONICS CO., LTD., Suwon-si (KR)

(72) Inventor: Geun-tae Bae, Anyang-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 536 days.

(21) Appl. No.: 15/314,555

(22) PCT Filed: Jun. 12, 2015

(86) PCT No.: PCT/KR2015/005948
§ 371 (c)(1),
(2) Date: Nov. 29, 2016

(87) PCT Pub. No.: WO2016/006834
PCT Pub. Date: Jan. 14, 2016

(65) Prior Publication Data
US 2017/0196531 A1 Jul. 13, 2017

(30) Foreign Application Priority Data
Jul. 11, 2014 (KR) .................. 10-2014-0087322

(51) Int. Cl.
*A61B 6/10* (2006.01)
*A61B 6/00* (2006.01)
*A61B 6/06* (2006.01)

(52) U.S. Cl.
CPC .................. *A61B 6/54* (2013.01); *A61B 6/06* (2013.01); *A61B 6/10* (2013.01); *A61B 6/4441* (2013.01);
(Continued)

(58) Field of Classification Search
CPC ...................................................... A61N 5/10
See application file for complete search history.

(56) References Cited

U.S. PATENT DOCUMENTS 7,523,350 B2   4/2009   Lintz, Jr. et al.
7,529,921 B2   5/2009   Stein et al.
(Continued)

FOREIGN PATENT DOCUMENTS

JP   11154099 A   6/1999
JP   11285494 A   10/1999
(Continued)

OTHER PUBLICATIONS

Communication dated Feb. 15, 2018, issued by the European Patent Office in counterpart European application No. 15818427.5.
(Continued)

*Primary Examiner* — Thomas R Artman
(74) *Attorney, Agent, or Firm* — Sughrue Mion, PLLC

(57) ABSTRACT

According to one or more exemplary embodiments, a medical imaging apparatus includes a first control unit. The first control unit controls capturing of an image of an object based on a first software component when the first software component is in an active state, periodically monitors a state of the first software component included in a software application, and sets any one of at least one second software component, which is the same as the first software component, to be in an active state when the first software component is in a failure state so as to continue to capture images of the object.

15 Claims, 11 Drawing Sheets

(52) U.S. Cl.
CPC .............. *A61B 6/461* (2013.01); *A61B 6/487* (2013.01); *A61B 6/563* (2013.01); *A61B 6/586* (2013.01)

(56) References Cited

U.S. PATENT DOCUMENTS

| | | | |
|---|---|---|---|
| 8,010,830 B2 | 8/2011 | Hotta et al. | |
| 8,201,017 B2 | 6/2012 | Koike et al. | |
| 8,392,748 B2 | 3/2013 | Bocharov et al. | |
| 9,326,742 B2* | 5/2016 | Hirschman | ............ G16H 20/17 |
| 10,016,618 B2* | 7/2018 | Hirschman | ............ G16H 20/17 |
| 2006/0005081 A1 | 1/2006 | Seth et al. | |
| 2008/0052313 A1 | 2/2008 | Keen | |
| 2008/0184219 A1* | 7/2008 | Matsumoto | ......... G06F 11/1433 |
| | | | 717/170 |
| 2010/0096679 A1 | 4/2010 | Park | |
| 2011/0013023 A1 | 1/2011 | Bailey et al. | |
| 2011/0178359 A1* | 7/2011 | Hirschman | ............ G16H 20/17 |
| | | | 600/4 |
| 2013/0227339 A1 | 8/2013 | Lund | |
| 2014/0040896 A1 | 2/2014 | Schmidt et al. | |
| 2016/0303397 A1* | 10/2016 | Hirschman | ............ G16H 20/17 |
| 2017/0196531 A1* | 7/2017 | Bae | ...................... A61B 6/4441 |

FOREIGN PATENT DOCUMENTS

| | | |
|---|---|---|
| JP | 11306000 A | 11/1999 |
| JP | 2004272505 A | 9/2004 |
| JP | 2008188161 A | 8/2008 |
| JP | 2008191773 A | 8/2008 |
| KR | 1020080063033 A | 7/2008 |
| KR | 101262278 B1 | 5/2013 |
| WO | 0019416 A2 | 4/2000 |

OTHER PUBLICATIONS

International Search Report and Written Opinion dated Sep. 8, 2015, issued by the International Searching Report in counterpart International Application No. PCT/KR2015/005948 (PCT/ISA/220, 210, & 237).

* cited by examiner

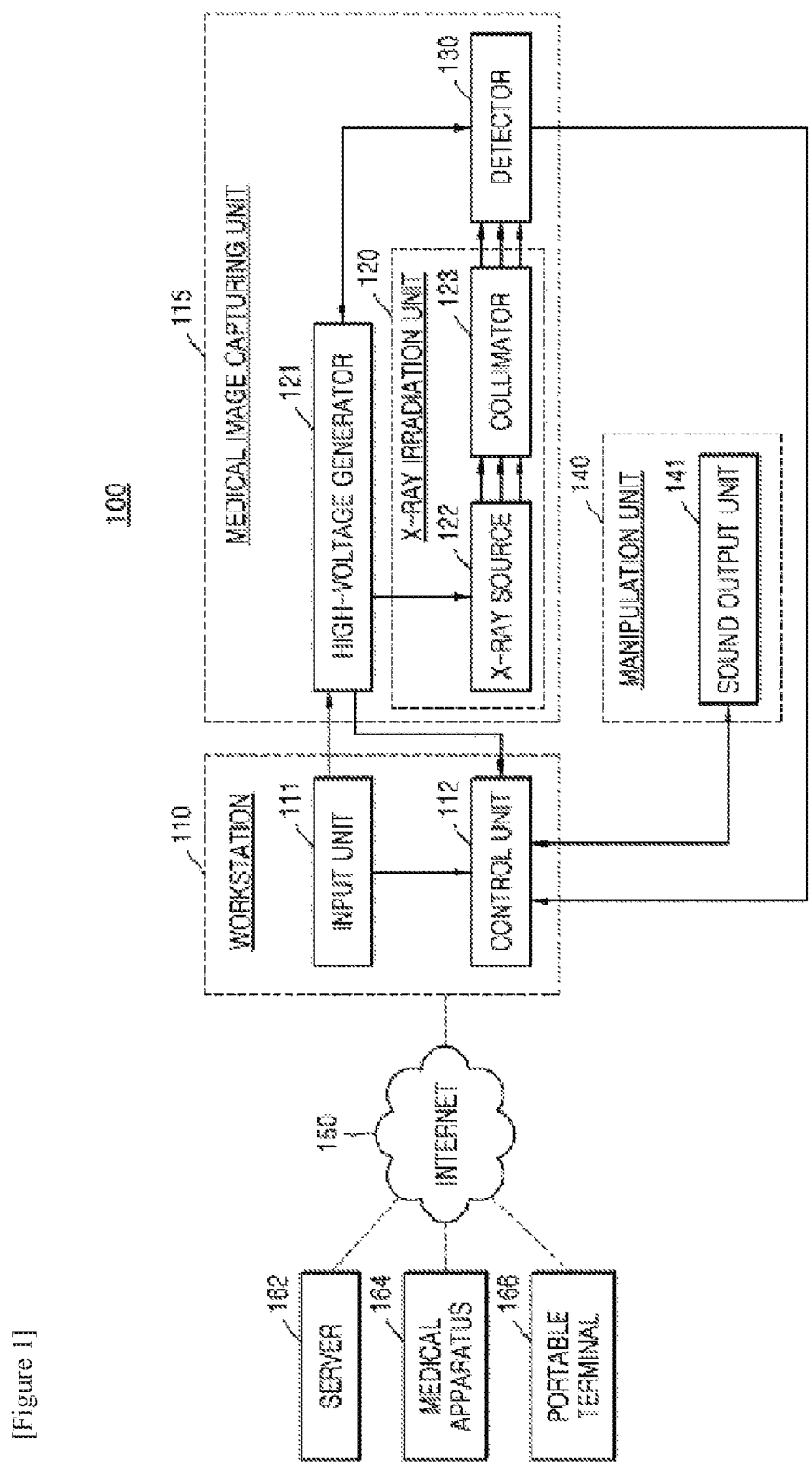
[Figure 1]

[Figure 2]
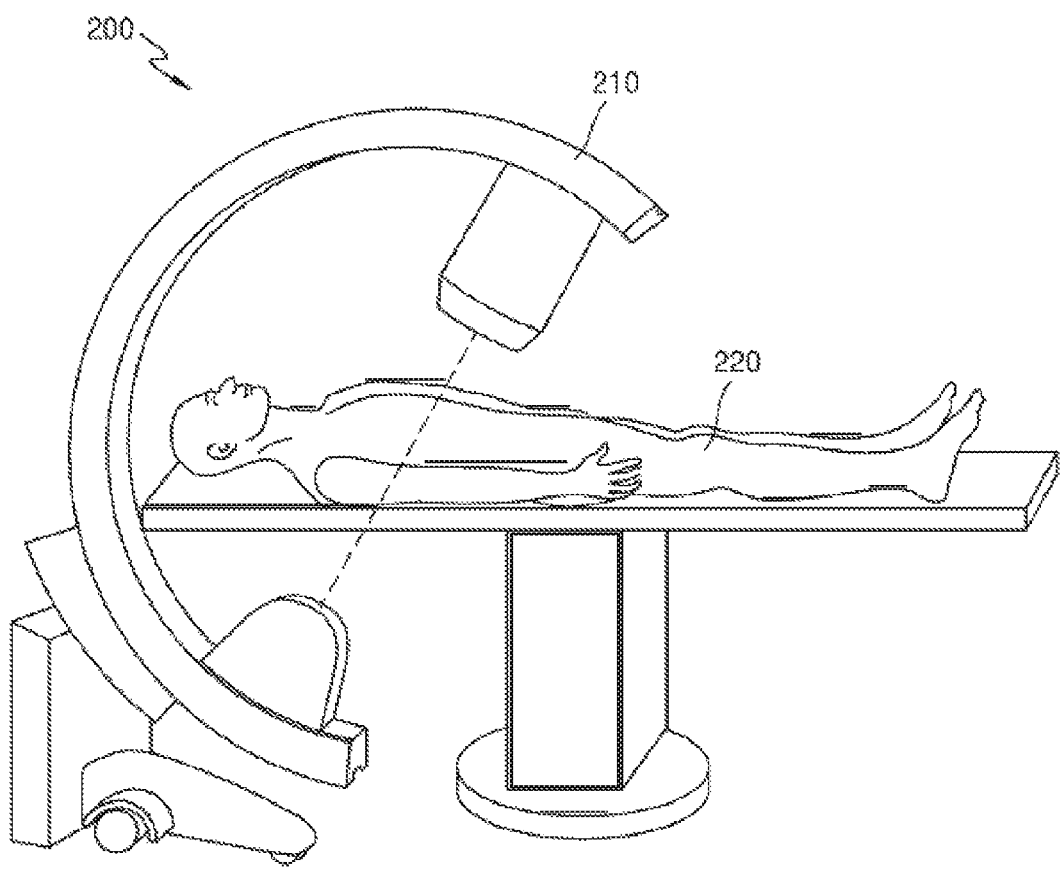

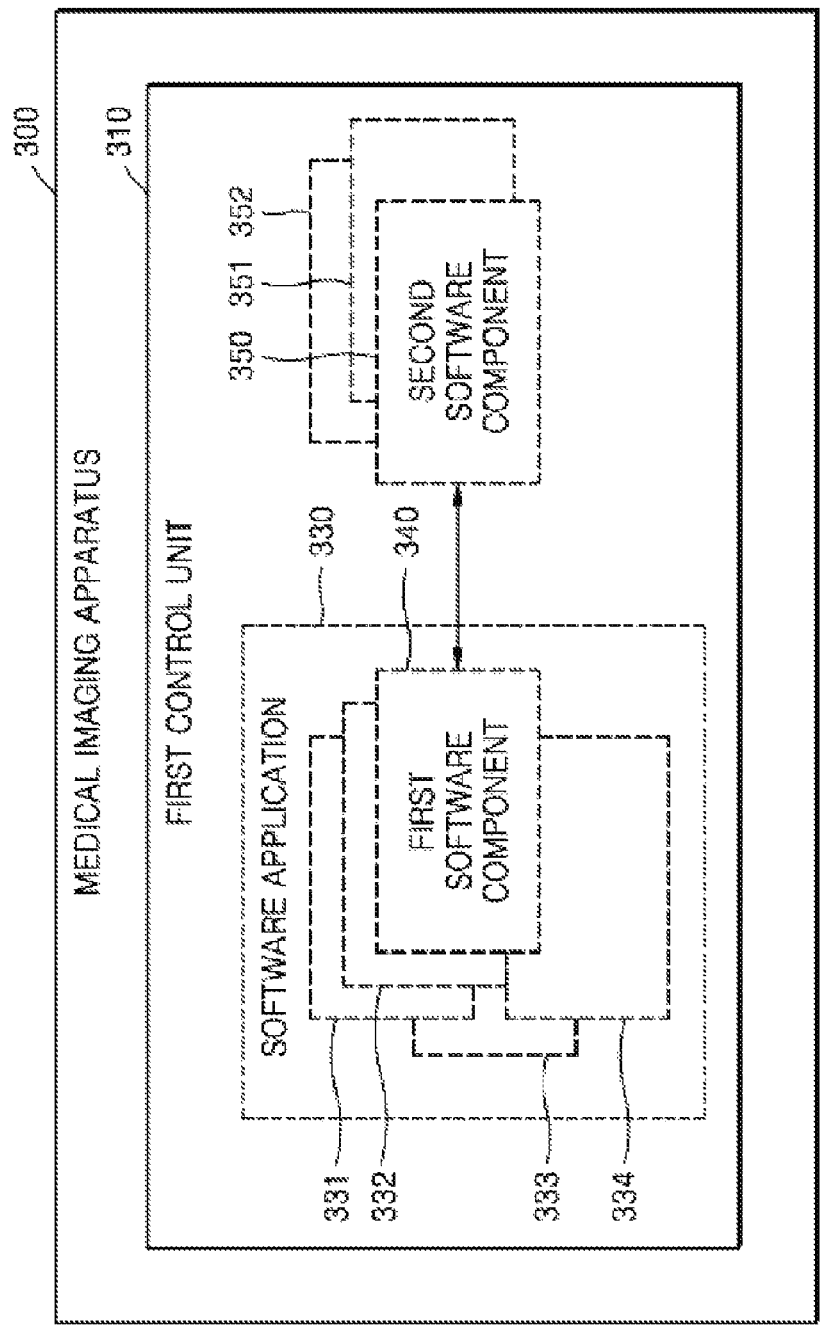
[Figure 3]

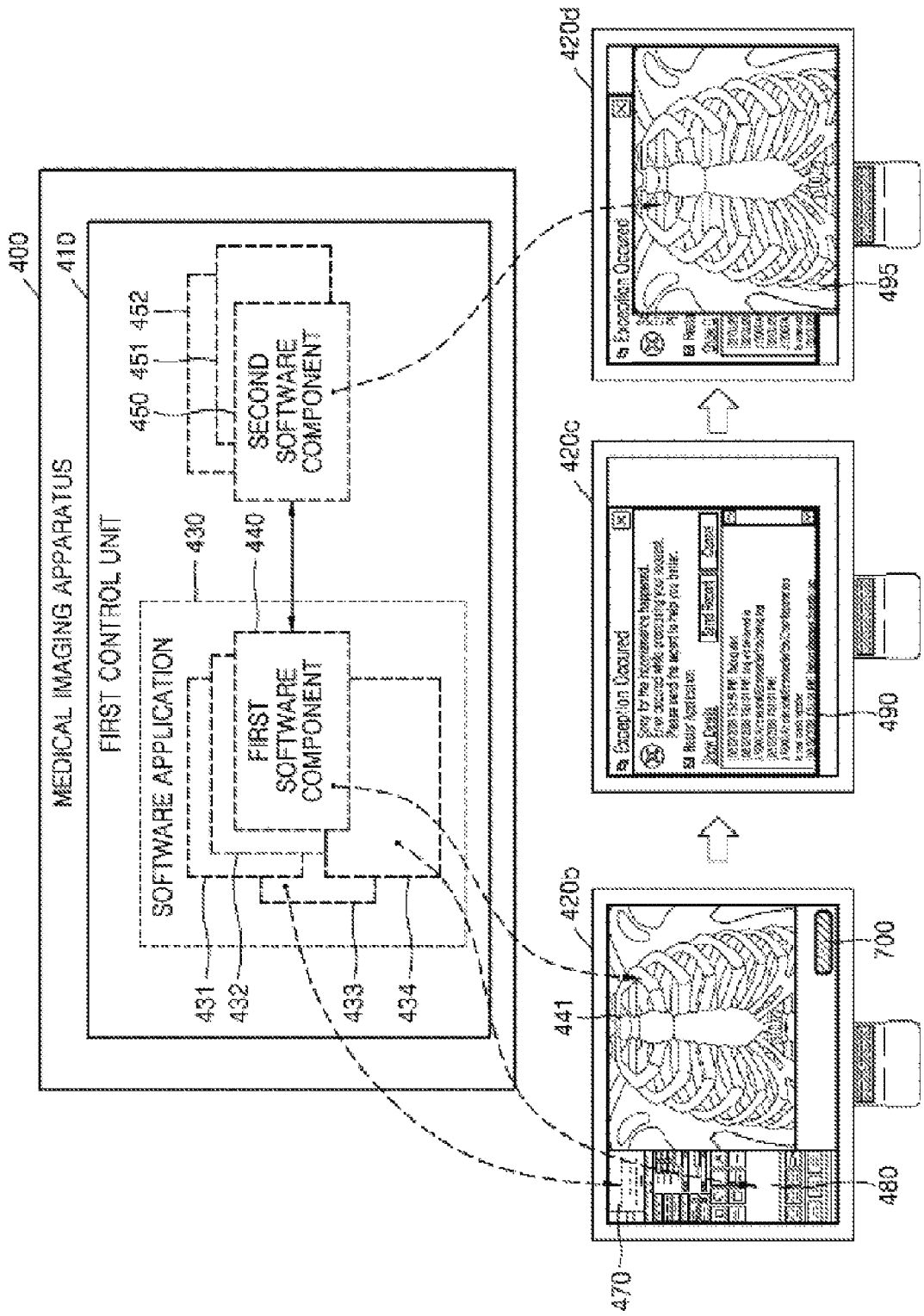
[Figure 4]

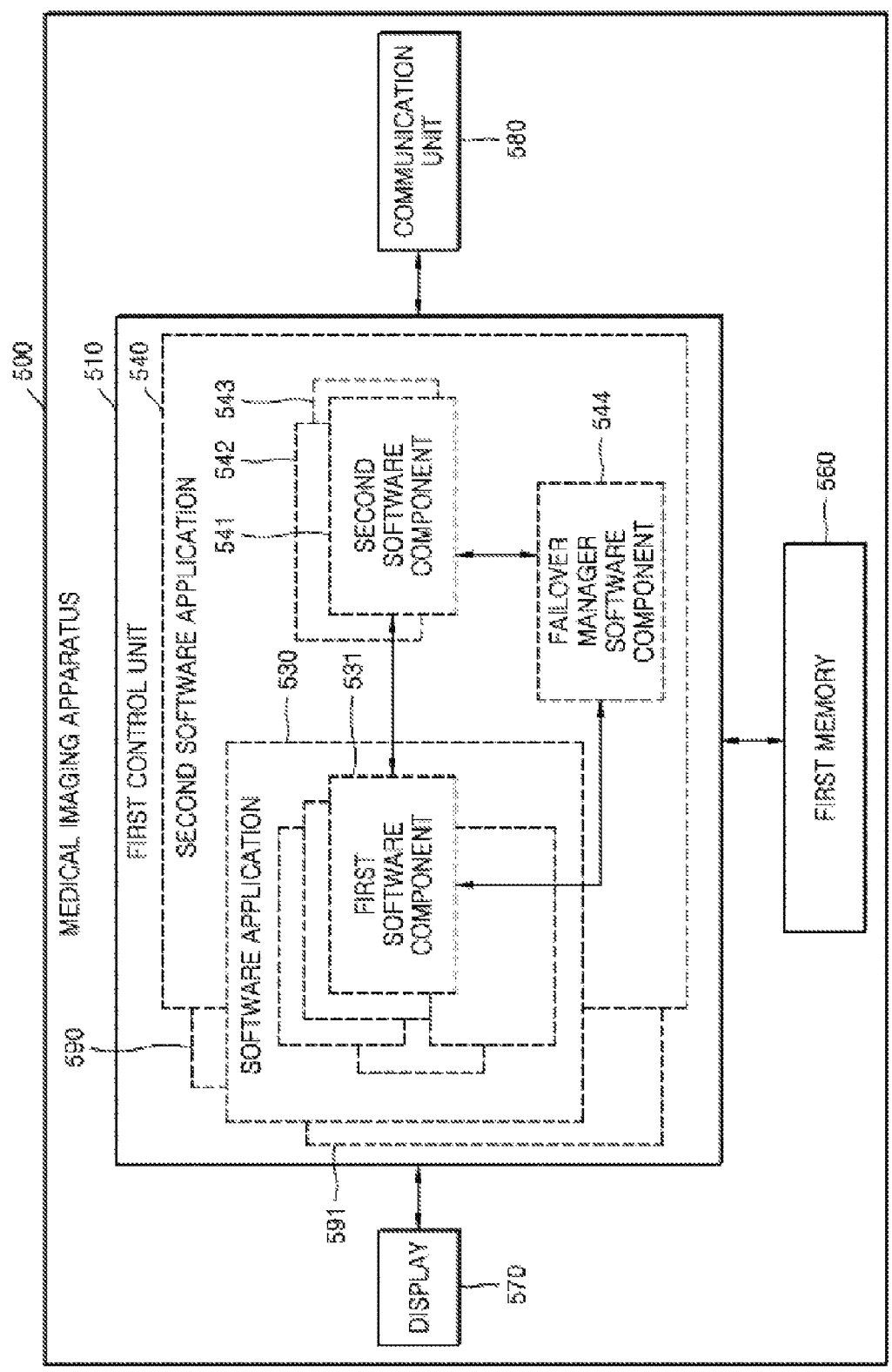

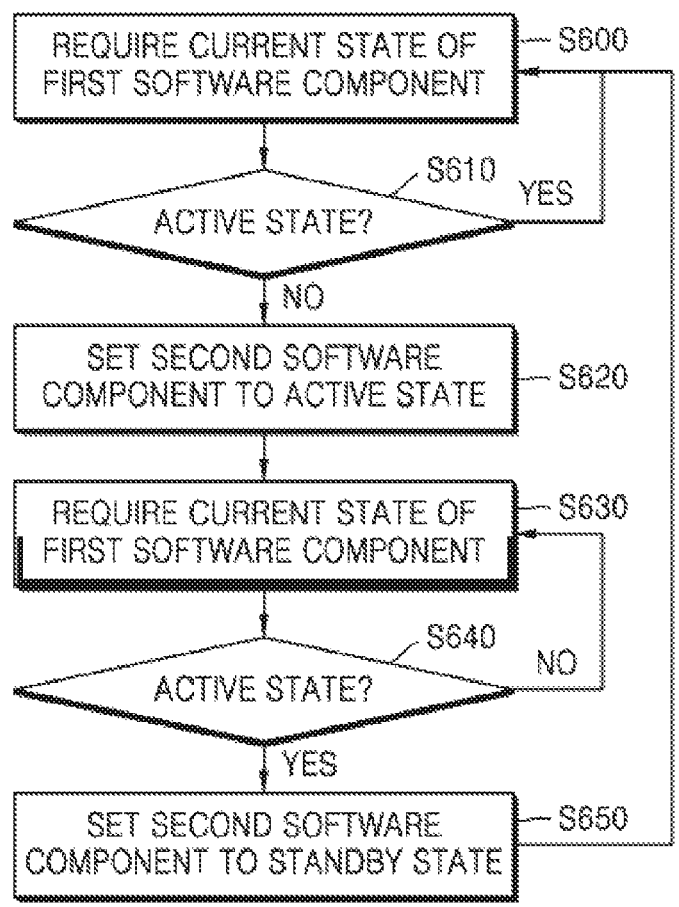
[Figure 6A]

[Figure 6B]
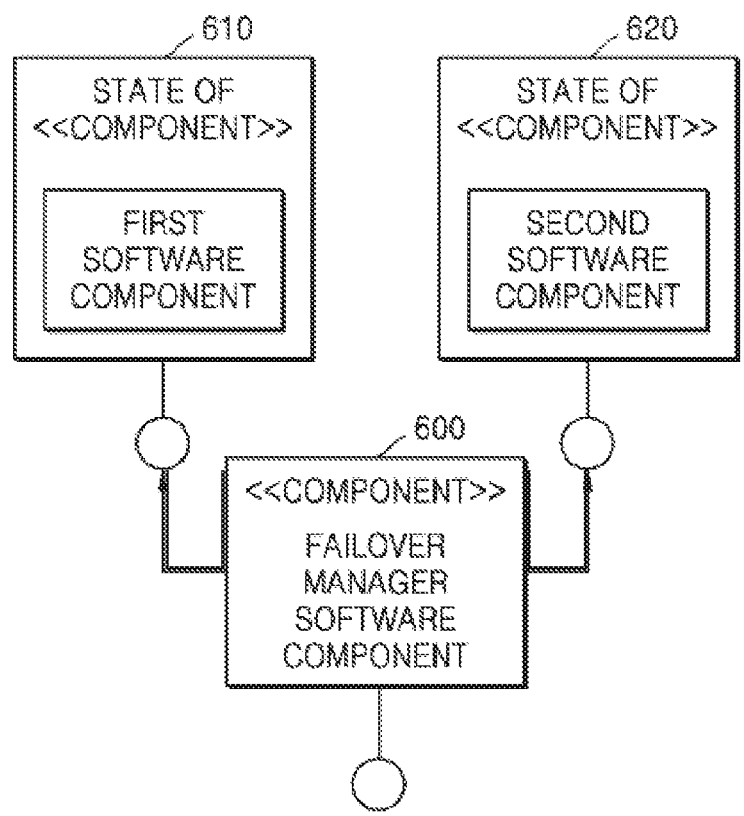

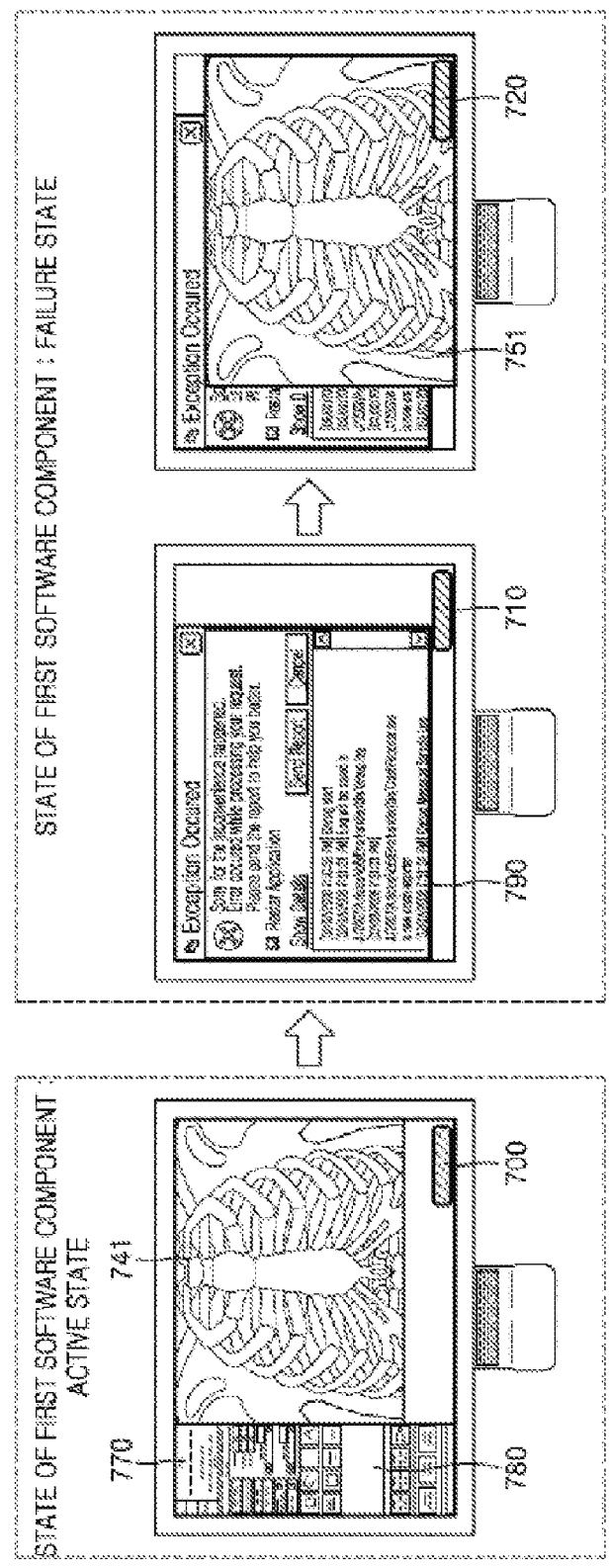
[Figure 7]

[Figure 8]
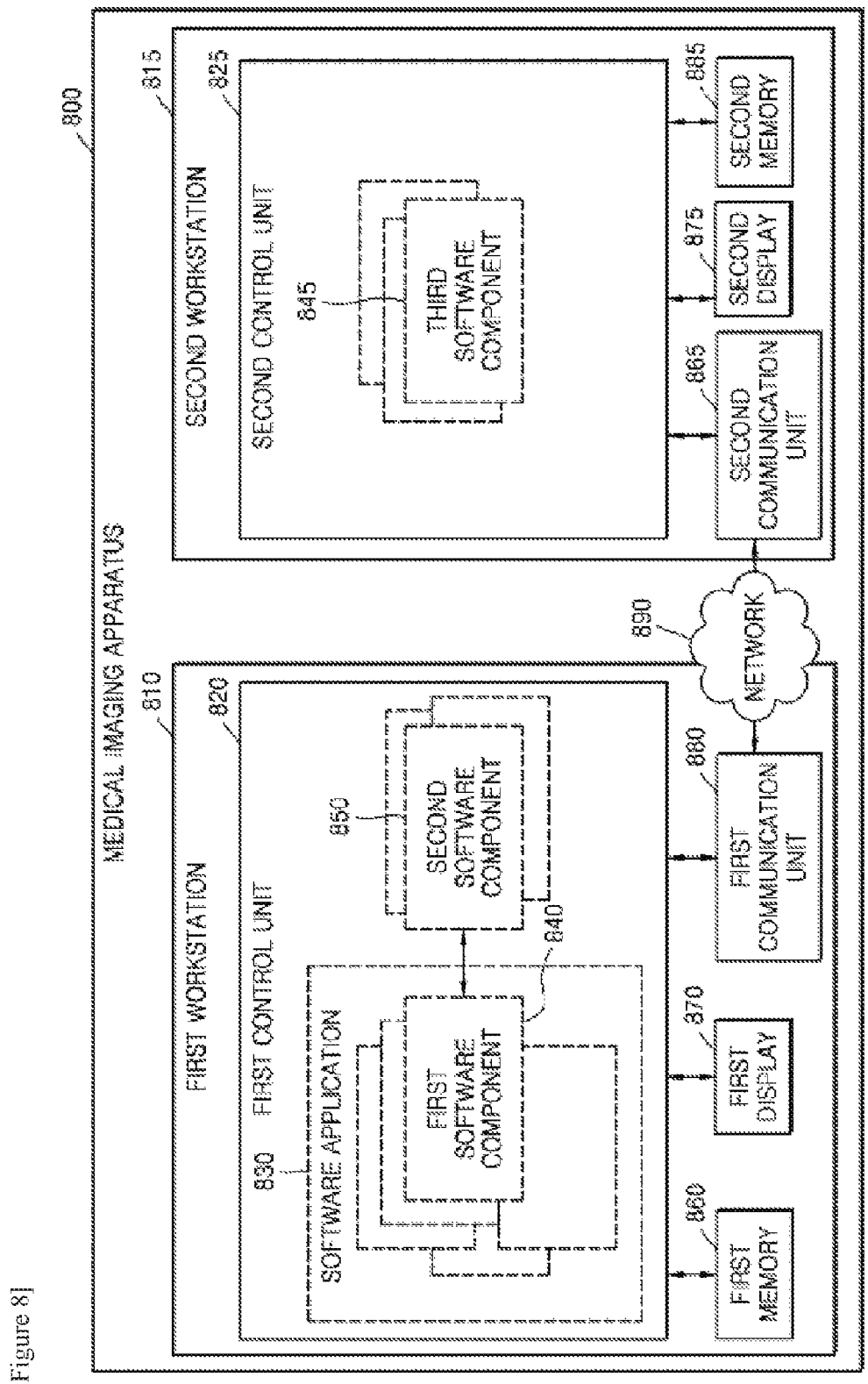

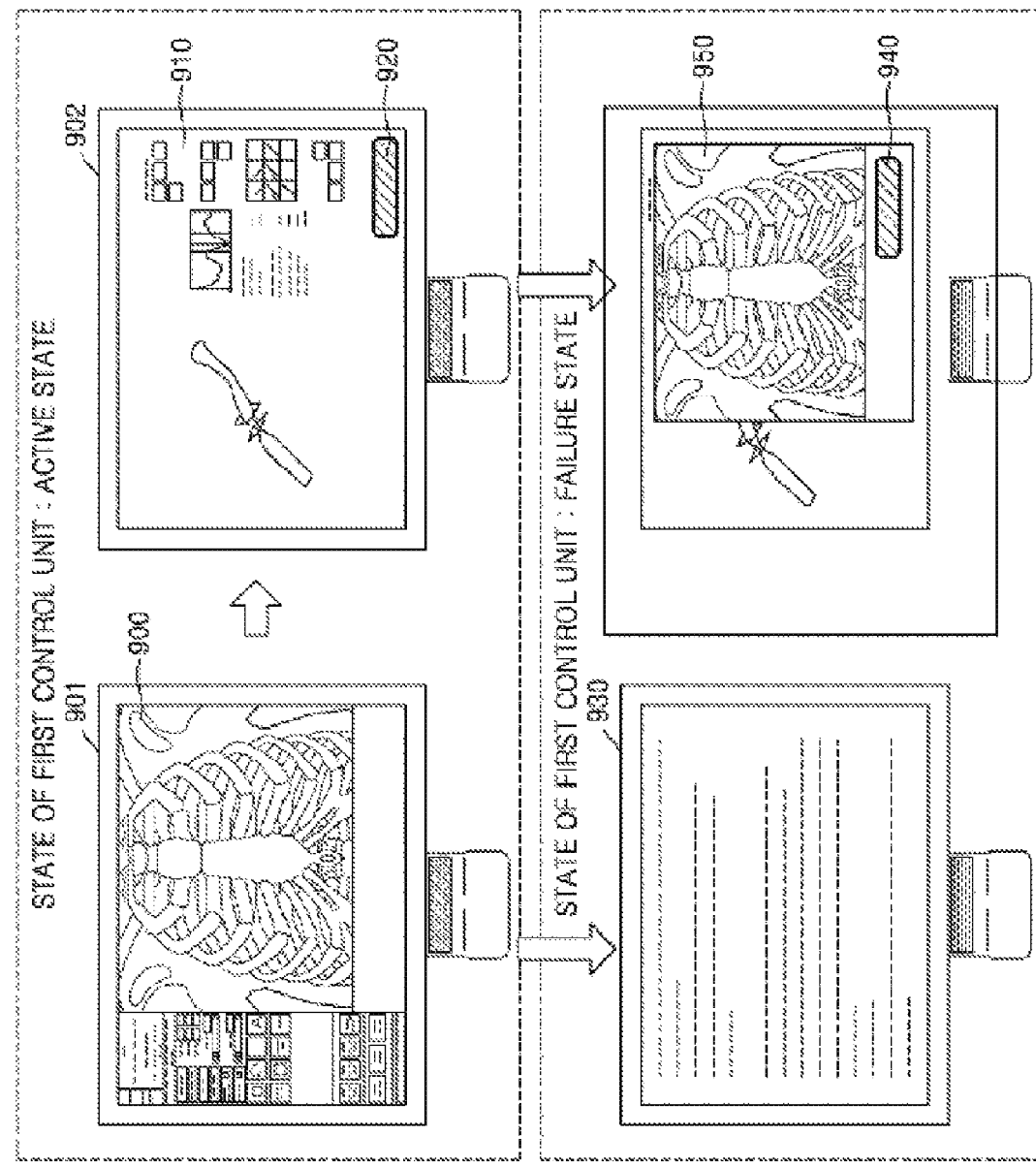

[Figure 10]
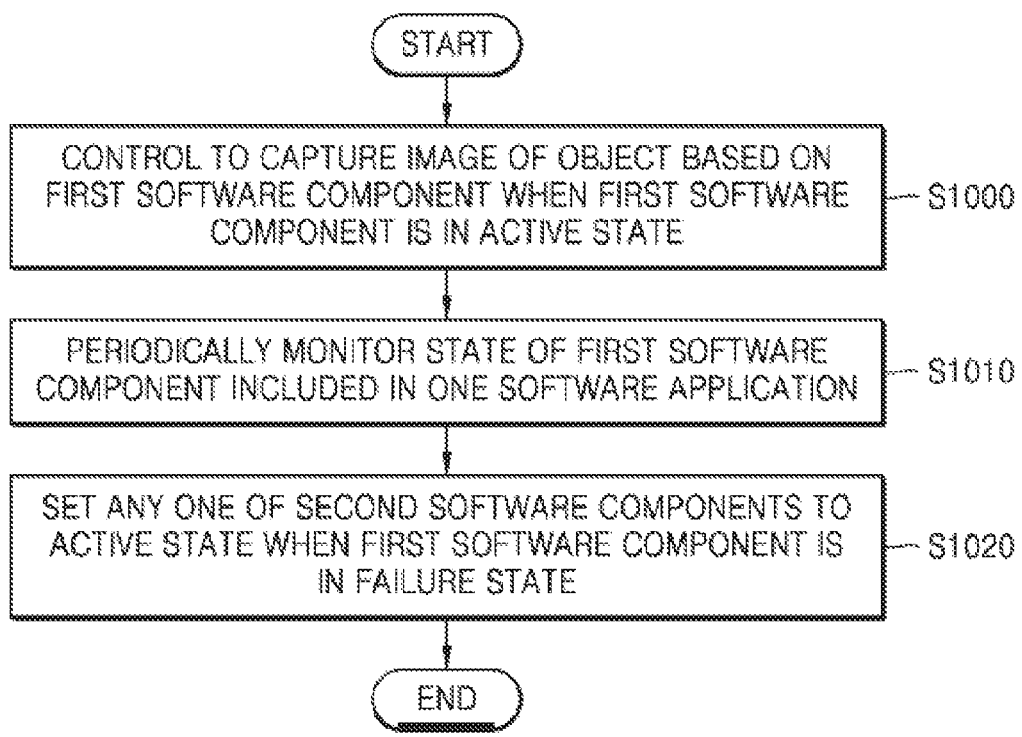

MEDICAL IMAGING APPARATUS AND METHOD OF SCANNING THEREOF

This application is a National stage entry of International Application No. PCT/KR2015/005948, filed on Jun. 12, 2015, which claims priority from Korean Patent Application No. 10-2014-0087322, filed on Jul. 11, 2014 in the Korean Intellectual Property Office. The disclosures of each of the applications are herein incorporated by reference in their entirety.

TECHNICAL FIELD

One or more exemplary embodiments relate to a medical imaging apparatus and method of performing failover with respect to a software component function.

BACKGROUND ART

When some or all of system functions have faults or failures, a fault-tolerant system performs a failover operation to failover the faulty system functions. The failover operation is usually used in a stability-critical system and a mission-critical system whose faults or failures may result in injuries to people or property damage. The failover operation is widely used in various fields such as atomic power generation, energy generation, national defense, aviation, space, vehicle, railroad, shipbuilding, plant industry, finance, and medical treatment.

The fault-tolerant system may use, for example, a redundancy or replication method using additional hardware devices. The redundancy or replication method is mainly applied to a large server system or a network system in which continuance of services needs to be ensured. Also, the redundancy or replication method is applied to some hardware devices forming a power supplier, a central processing unit (CPU), a memory, a hard drive, etc. in order to prevent a single point of failure.

In detail, according to the redundancy or replication method, although hardware, which is critical to provide the services, or a single element stops operating or has a fault, an object which is the same as the hardware or the single element starts operating, and thus, the services may continue to be provided.

However, according to technology of the related art, some portions or an entire portion of hardware forming a system, for example, a computing server, a network switch, components, etc. are replicated to prevent a halt of an entire system.

Therefore, a fault-tolerant system capable of selectively replicating predetermined functions requiring continuity or stability is necessary.

DISCLOSURE

Technical Solution

According to one or more exemplary embodiments, a medical imaging apparatus includes a first control unit. The first control unit controls capturing of an image of an object based on a first software component when the first software component is in an active state, periodically monitors a state of the first software component included in a software application, and sets any one of at least one second software component, which is the same as the first software component, to be in an active state when the first software component is in a failure state so as to continue to capture images of the object.

Advantageous Effects

One or more exemplary embodiments include a medical imaging apparatus capable of performing failover with respect to predetermined functions thereof based on a software component. In particular, when predetermined functions requiring continuity and stability have faults, a medical imaging apparatus capable of performing failover with respect to a software component performing the predetermined functions is provided.

Additional aspects will be set forth in part in the description which follows and, in part, will be apparent from the description, or may be learned by practice of the presented exemplary embodiments.

DESCRIPTION OF DRAWINGS

These and/or other aspects will become apparent and more readily appreciated from the following description of the exemplary embodiments, taken in conjunction with the accompanying drawings in which:

FIG. 1 is a block diagram of an X-ray apparatus according to an exemplary embodiment;

FIG. 2 illustrates a C-arm X-ray apparatus according to an exemplary embodiment;

FIG. 3 is a block diagram of a structure of a medical imaging apparatus according to an exemplary embodiment;

FIG. 4 is a view for explaining operations of a medical imaging apparatus according to an exemplary embodiment;

FIG. 5 is a block diagram of a structure of a medical imaging apparatus according to another exemplary embodiment;

FIGS. 6A and 6B respectively are a flowchart and a block diagram for explaining operations of a medical imaging apparatus according to another exemplary embodiment;

FIG. 7 illustrate operations of a medical imaging apparatus according to another exemplary embodiment;

FIG. 8 is a block diagram of a structure of a medical imaging apparatus according to another exemplary embodiment;

FIG. 9 illustrate operations of a medical imaging apparatus according to another exemplary embodiment; and FIG. 10 is a flowchart of a method of capturing a medical image by using a medical imaging apparatus, according to an exemplary embodiment.

BEST MODE

According to one or more exemplary embodiments, a medical imaging apparatus includes a first control unit. The first control unit controls capturing of an image of an object based on a first software component when the first software component is in an active state, periodically monitors a state of the first software component included in a software application, and sets any one of at least one second software component, which is the same as the first software component, to be in an active state when the first software component is in a failure state so as to continue to capture images of the object.

The first software component may be separable from the software application.

The software application may include a plurality of software components, the plurality of software components may independently operate and are separable from the software application, and the first software component may be any one of the plurality of software components.

The medical imaging apparatus may further include a first memory including the at least one second software component. The first control unit may set the at least one second software component included in the first memory to be in a standby state and sets any one of the at least one second software component, which is set to be in the standby state, to be in an active state when the first software component is in the failure state so that the images of the object continue to be captured.

The first control unit may periodically acquire at least one piece of state information included in the first software component and may set any one of the at least one second software component, which is set to be in the standby state, to be in an active state based on the at least one acquired piece of state information when the first software component is in the failure state.

The first control unit may set the at least one second software component, which is set be to in the active state, to be in a standby state when the first software component, which has been in the failure state, is set to be in an active state.

The first software component may control capturing of a fluoroscopy image or acquire a fluoroscopy image.

The first software component may control capturing of a fluoroscopy image or acquire a fluoroscopy image, and the state information may include at least one of conditions for capturing the fluoroscopy image, user setting information, and a current state of the software application.

The medical imaging apparatus may further include: a second memory loading at least one third software component which is the same as the first software component; and a second control unit setting the at least one third software component loaded in the second memory to be in a standby state when the first control unit is in the active state and sets any one of the at least one third software component, which is set to be in the standby state, to be in an active state when the first control unit is in a failure state so that the capturing may be controlled to continue being performed.

The second control unit may periodically acquire at least one piece of state information included in the first software component or in the at least one second software component and may set any one of the at least one third software component, which is set to be in the standby state, to be in an active state based on the at least one acquired piece of state information when the first control unit is in the failure state so that the capturing is controlled to continue being performed.

The medical imaging apparatus may further include: a first workstation including the first control unit and the first memory; and a second workstation including the second control unit and the second memory. The first workstation and the second workstation may be hardware devices which are independent from each other.

The medical imaging apparatus may further include a medical image capturing unit capturing medical images of the object.

According to one or more exemplary embodiments, a method of capturing a medical image by using a medical imaging apparatus, includes: controlling an object to be captured based on a first software component when the first software component is in an active state; periodically monitoring a state of the first software component included in a software application; and controlling capturing of an image of the object by setting any one of at least one second software component which is the same as the first software component to be in an active state when the first software component is in a failure state.

The method may further include: loading the at least one second software component in a first memory; and setting the at least one second software component loaded in the first memory to be in a standby state when the first software component is in the active state. The controlling of the capturing may include setting any one of the at least one second software component, which is set to be in the standby state, to be in an active state when the first software component is in the failure state so that the images of the object may continue to be captured.

The method may further include periodically acquiring at least one piece of state information included in the first software component. The controlling of the capturing may include setting any one of the at least one second software component, which is set to be in the standby state, to be in an active state based on the at least one acquired piece of state information when the first software component is in the failure state.

The first software component may control capturing of a fluoroscopy image or acquire a fluoroscopy image.

The first software component may control capturing of a fluoroscopy image or acquire a fluoroscopy image. The state information may include at least one of conditions for capturing the fluoroscopy image, user setting information, and a current state of the software application.

According to one or more exemplary embodiments, there is provided a non-transitory computer-readable recording medium having embodied thereon a computer program for executing the above method.

Mode for Invention

This application claims the benefit of Korean Patent Application No. 10-2014-0087322, filed on Jul. 11, 2014, in the Korean Intellectual Property Office, the disclosure of which is incorporated herein in its entirety by reference.

Advantages and features of one or more exemplary embodiments of the inventive concept and methods of accomplishing the same may be understood more readily by reference to the following detailed description of the exemplary embodiments and the accompanying drawings. In this regard, the present exemplary embodiments may have different forms and should not be construed as being limited to the descriptions set forth herein. Rather, these exemplary embodiments are provided so that this disclosure will be thorough and complete and will fully convey the concept of the present exemplary embodiments to one of ordinary skill in the art, and the inventive concept will only be defined by the appended claims.

Hereinafter, the terms used in the specification will be briefly described, and then the inventive concept will be described in detail.

The terms used in this specification are those general terms currently widely used in the art in consideration of functions regarding the inventive concept, but the terms may vary according to the intention of those of ordinary skill in the art, precedents, or new technology in the art. Also, some terms may be arbitrarily selected by the applicant, and in this case, the meaning of the selected terms will be described in detail in the detailed description of the present specification. Thus, the terms used in the specification should be understood not as simple names but based on the meaning of the terms and the overall description of the invention.

Throughout the specification, an "image" may denote multi-dimensional data composed of discrete image elements (for example, pixels in a two-dimensional image and voxels in a three-dimensional image). For example, an image may include medical images of an object acquired by an X-ray, a CT, an MRI, an ultrasound wave, and other medical image systems.

Furthermore, in the present specification, an "object" may be a human, an animal, or a part of a human or animal. For example, the object may be an organ (e.g., the liver, the heart, the womb, the brain, a breast, or the abdomen), a blood vessel, or a combination thereof. Furthermore, the "object" may be a phantom. The phantom means a material having a density, an effective atomic number, and a volume that are approximately the same as those of an organism. For example, the phantom may be a spherical phantom having properties similar to the human body.

Furthermore, in the present specification, a "user" may be, but is not limited to, a medical expert, such as a medical doctor, a nurse, a medical laboratory technologist, or a technician who repairs a medical apparatus.

An X-ray apparatus is a medical imaging apparatus that acquires images of internal structures of an object by transmitting an X-ray through the human body. The X-ray apparatus may acquire medical images of an object more simply within a shorter time than other medical imaging apparatuses including an MRI apparatus and a CT apparatus. Therefore, the X-ray apparatus is widely used in simple chest photographing, simple abdomen photographing, simple skeleton photographing, simple nasal sinuses photographing, simple neck soft tissue photographing, and breast photographing.

FIG. 1 is a block diagram of an X-ray apparatus 100. The X-ray apparatus 100 shown in FIG. 1 may be a fixed-type X-ray apparatus or a mobile X-ray apparatus.

Referring to FIG. 1, the X-ray apparatus 100 includes a workstation 110 and a medical image capturing unit 115.

The workstation 110 includes an input unit 111 through which a user may input commands for manipulating the X-ray apparatus 100 including an X-ray irradiation, and a control unit 112 controlling overall operations of the X-ray apparatus 100.

The medical image capturing unit 115 may include a high voltage generator 121, an X-ray irradiation unit 120, and a detector 130.

The high voltage generator 121 generates a high voltage for generating X-rays, and applies the high voltage to an X-ray source 122.

The X-ray irradiation unit 120 includes the X-ray source 122 receiving the high voltage applied from the high voltage generator 121 to generate and irradiate the X-ray, and a collimator 123 for guiding a path of the X-ray irradiated from the X-ray source 122.

The detector 130 detects the X-ray that is irradiated by the X-ray irradiation unit 120 and penetrates the object.

Also, the X-ray apparatus 100 may further include a manipulation unit 140 including a sound output unit 141 outputting sound representing information relating to photographing operation such as the X-ray irradiation under a control of the control unit 112.

The workstation 110, the X-ray irradiation unit 120, the high voltage generator 121, and the detector 130 may be connected to each other via wires or wirelessly. If they are connected to each other wirelessly, a device (not shown) for synchronizing clocks with each other may be further included.

The input unit 111 may include a keyboard, a mouse, a touch screen, a voice recognizer, a fingerprint recognizer, an iris recognizer, and the like well known in the art. The user may input a command for irradiating the X-ray via the input unit 111, and to do this, the input unit 111 may include a switch for inputting the command. The switch may be configured so that an irradiation command for irradiating the X-ray may be input only when the switch is pushed twice.

In other words, when the user pushes the switch, a prepare command for performing a pre-heating operation for X-ray radiation may be input, and in this state, when the user pushes the switch deeper, a radiation command for performing substantial X-ray radiation may be input. When the user manipulates the switch as described above, the input unit 111 generates signals corresponding to the commands input through the switch manipulation, that is, a prepare signal and an irradiation signal, and outputs the generated signals to the high voltage generator 121 generating a high voltage for generating the X-ray.

When the high voltage generator 121 receives the prepare signal output from the input unit 111, the high voltage generator 121 starts a pre-heating operation, and when the pre-heating is finished, the high voltage generator 121 outputs a ready signal to the control unit 121. In addition, the detector 130 also needs to prepare for detecting the X-ray, and thus, when the high voltage generator 121 receives the prepare signal output from the input unit 111, the high voltage generator 121 outputs a prepare signal to the detector 130 at the same time of performing the pre-heating operation, so that the detector 130 may prepare for detecting the X-ray transmitted through the object. The detector 130 prepares for detecting the X-ray when receiving the prepare signal, and when the preparing for the detection is finished, the detector 130 outputs a ready signal to the high voltage generator 121 and the control unit 112.

When the pre-heating operation of the high voltage generator 121 is finished, the detector 130 is ready for the detecting the X-ray, and the irradiation signal is output from the input unit 111 to the high voltage generator 121, the high voltage generator 121 generates and applies the high voltage to the X-ray source 122, and the X-ray source 122 irradiates the X-ray.

When the irradiation signal is output from the input unit 111, the control unit 112 may output a sound output signal to the sound output unit 141 so that the sound output unit 141 outputs predetermined sound and the object may recognize the irradiation of X-ray. Also, the sound output unit 141 may output sound representing other information relating to the photographing, in addition to the X-ray irradiation. In FIG. 1, the sound output unit 141 is included in the manipulation unit 140; however, the exemplary embodiments of the inventive concept are not limited thereto, and the sound output unit 140 may be located at a different location from the manipulation unit 140. For example, the sound output unit 141 may be included in the workstation 110, or may be located on a wall surface of an examination room in which the X-ray photographing of the object is performed.

The control unit 112 controls locations of the X-ray irradiation unit 120 and the detector 130, a photographing timing, and photographing conditions according to photographing conditions set by the user.

In more detail, the control unit 112 controls the high voltage generator 121 and the detector 130 according to the command input via the input unit 111 so as to control an irradiation timing of the X-ray, an intensity of the X-ray, and an irradiation region of the X-ray. Also, the control unit 112 adjusts the location of the detector 130 according to a predetermined photographing condition, and controls an operation timing of the detector 130.

In addition, the control unit 112 generates a medical image of the object by using image data transmitted from the detector 130. In detail, the control unit 121 receives the image data from the detector 130, and then, generates the medical image of the object by removing noise in the image data, and adjusting a dynamic range and interleaving of the image data.

The X-ray apparatus 100 shown in FIG. 1 may further include an output unit (not shown) for outputting the medical image generated by the control unit 112. The output unit may output information that is necessary for the user to manipulate the X-ray apparatus 100, for example, a user interface (UI), user information, or object information. The output unit may include a printer, a cathode ray tube (CRT) display, a liquid crystal display (LCD), a plasma display panel (PDP), an organic light emitting diode (OLED) display, a field emission display (FED), a light emitting diode (LED) display, a vacuum fluorescent display (VFD), a digital light processing (DLP) display, a primary flight display (PFD), a three-dimensional (3D) display, a transparent display, and other various output devices well known in the art.

The workstation 110 shown in FIG. 1 may further include a communication unit (not shown) that may be connected to a server 162, a medical apparatus 164, and a portable terminal 166 via a network 150.

The communication unit may be connected to the network 150 via wires or wirelessly to communicate with the external server 162, the external medical apparatus 164, or the external portable terminal 166. The communication unit may transmit or receive data relating to diagnosis of the object via the network 150, and may transmit or receive medical images captured by the other medical apparatus 164, for example, a CT, an MRI, or an X-ray apparatus. Moreover, the communication unit may receive medical history or treatment schedule of an object (e.g., a patient) from the server 162 to diagnose a disease of the object. Also, the communication unit may perform data communication with the portable terminal 166 such as a mobile phone of a doctor or a patient, a personal digital assistant (PDA), or a laptop computer, as well as the server 162 or the medical apparatus 164 in a hospital.

The communication unit may include one or more elements enabling to communicate with external apparatuses, for example, a short distance communication module, a wired communication module, and a wireless communication module.

The short distance communication module is a module for communicating with a device located within a predetermined distance. The short distance communication technology may be wireless local area network (LAN), Wi-Fi, Bluetooth, Zigbee, Wi-Fi Direct (WFD), ultra wideband (UWD), infrared data association (IrDA), Bluetooth low energy (BLE), near field communication (NFC), or the like; however, the exemplary embodiments of the inventive concept are not limited thereto.

The wired communication module is a module for communicating by using an electric signal or an optical signal, and the wired communication technology may be wired communication technology using a pair cable, a coaxial cable, or an optical fiber cable, and a wired communication technology that is well known in the art.

The wireless communication module may transmit/receive a wireless signal to/from at least one of a base, an external device, and a server in a mobile communication network. Here, the wireless signal may be a voice call signal, a video call signal, or various types of data according to text/multimedia messages transmission. The X-ray apparatus 100 shown in FIG. 1 may include a plurality of digital signal processors (DSPs), an ultra-small calculator, and a processing circuit for specialized usage (for example, a high speed analog/digital (A/D) conversion, a high speed Fourier transformation, an array process, etc.).

In addition, the communication between the workstation 110 and the X-ray generator 120, the workstation 110 and the high voltage generator 211, and the workstation 110 and the detector 130 may use a high speed digital interface, such as low voltage differential signalling (LVDS), asynchronous serial communication, such as universal asynchronous receiver transmitter (UART), synchronous serial communication, or a low latency network protocol, such as a control unit area network (CAN), and other various communication methods that are well known in the art may be used.

FIG. 2 illustrates a C-arm X-ray apparatus 200 according to an exemplary embodiment.

The user may capture an image of an object 220 at various locations or angles by using a C-arm 210. For example, the user may rotate or move the C-arm 210 in a vertical or horizontal direction in order to capture an image of a region of interest (ROI) of the object 220, and thus, the user may acquire a fluoroscopy image. Accordingly, the user uses the C-arm X-ray apparatus 200 to more effectively capture an image of the object 220 than a fixed-type X-ray apparatus of the related art. A structure of the C-arm X-ray apparatus 200 is well known to one of ordinary skill in the art, and thus, detailed descriptions thereof will be omitted.

The C-arm X-ray apparatus 200 may be usefully employed during medical procedures such as X-ray angiography or a surgical operation. During the medical procedures, the user needs to keep checking an X-ray image of the object 220 and to acquire a fluoroscopy image thereof by continuously irradiating the X-ray on the object 220.

As an example, in the case of the angiography, guide wires are installed around the object 220 or medicines are injected using a thin needle, etc. so as to capture an X-ray image.

As another example, in the case of the surgical operation, when an operation is performed by inserting a catheter, a stent, a needle, or the like into a human body, a user such as a doctor needs to check whether the catheter, the stent, the needle, or the like is properly inserted into a target location of the human body. Therefore, the user may acquire the fluoroscopy image and may check a location of a target such as a catheter by using the acquired fluoroscopy image, and thus, the user may perform the medical procedures.

If an error such as an unexpected halt of the medical imaging apparatus occurs when a medical imaging apparatus is used to support an invasive operation, or when medical images need to be continuously captured in real time, patients may be fatally affected. For example, since a surgical operation or surgery may stop being performed, a case of medical malpractice may occur. Therefore, one or more exemplary embodiments of the inventive concept may be applied to a medical imaging apparatus configured to support an invasive operation or to continuously capture medical images in real time.

In addition, one or more exemplary embodiments of the inventive concept may be applied to a medical imaging apparatus in order to prevent the additional occurrence of radiation exposure by operating the medical imaging apparatus without a halt.

For example, one or more exemplary embodiments of the inventive concept may be applied to a C-arm X-ray apparatus configured to support an invasive operation such as angiography. In detail, when a fluoroscopy image of an object is captured by the C-arm X-ray apparatus after a medical tool such as guide wires, a needle, a catheter, or a stent is inserted into the object, one or more exemplary embodiments of the inventive concept may be applied to secure continuity and stability of the fluoroscopy image. In detail, a medical imaging apparatus 300 of FIG. 3 may be included in the workstation 110 of FIG. 1 or a workstation (not shown) of the C-arm X-ray apparatus 200 of FIG. 2.

In the related art with regard to a fault-tolerant system, a number of hardware devices are used. That is, a plurality of hardware systems which perform the same functions and are interchangeable with each other are additionally included. In detail, when some or all of functions of a system have faults, the interchangeable hardware systems may be used to failover the system. In the related art, a failover method has been applied to various hardware devices such as a server computer, a network switch (a router), a central processing unit (CPU), random access memory (RAM), and a hard disk. The failover method may be referred to as a redundancy or replication method.

However, according to the related art, since additional hardware is necessary, costs are increased, and managing becomes more complicated. In particular, when a unit of predetermined hardware to which the redundancy method is applied is large, or when hardware forming a system is entirely replicated, costs are increased.

A medical imaging apparatus capable of performing failover with respect to predetermined functions, which require continuity and stability, by using existing hardware without preparation of additional hardware as in the related art, may be provided.

In detail, the medical imaging apparatus according to one or more exemplary embodiments of the inventive concept may replicate the software components to form the fault-tolerant system. The software component may indicate a software package or a software module which encapsulates predetermined separate functions or a plurality of functions. The software component may be separable, replaceable, or reusable.

In particular, the term 'separable' means that an algorithm or code corresponding to a software component is easily separable from another algorithm or code. For example, a code of the software component may be easily separated from codes of a software application. Also, the term may mean that a function performed by the software component may be independently implemented on a system. However, although the software component is separable from a function, the function may be closely related to another function in consideration of the entire system. Therefore, the plurality of software components may be closely connected to each other.

Also, the software component may be replaced with another software component performing the same function and having the same structure and may also be reused in another software program.

In addition, a designer may easily design a software program including a software component based on a software development methodology such as Component Based Development (CBD).

The software component concept is well known to one of ordinary skill in the art, and thus, detailed descriptions of a software component structure will be omitted.

Also, the software component may be an element of a software program, an application program, or a software application which is configured to perform a certain task. Hereinafter, a software system including a software program and an application program and designed based on a software component in order to perform a certain task will be referred to as the "software application".

Hereinafter, a medical imaging apparatus which may perform failover with respect to predetermined functions based on the software component will be described in detail.

FIG. 3 is a block diagram of a structure of the medical imaging apparatus 300 according to an exemplary embodiment.

The medical imaging apparatus 300 may include a first control unit 310.

The medical imaging apparatus 300 may be included in an apparatus capable of capturing an image of an object, for example, an X-ray apparatus, a computed tomography (CT) apparatus, a magnetic resonance imaging (MRI) apparatus, and an ultrasonic apparatus, which is configured to examine an object or support a surgery.

In detail, when the medical imaging apparatus 300 of FIG. 3 is included in the X-ray apparatus 100 of FIG. 1, the medical imaging apparatus 300 may correspond to the workstation 110 and the control unit 112 of FIG. 1. The first control unit 310 of FIG. 3 may correspond to the control unit 112 of FIG. 1. Therefore, repeated descriptions thereof will be omitted.

The medical imaging apparatus 300 may further include a medical image capturing unit (not shown). That is, according to photographing conditions set by the user, the first control unit 310 controls a photographing timing or photographing conditions of the medical image capturing unit, and the medical image capturing unit captures a medical image of the object.

For example, when the medical imaging apparatus 300 of FIG. 3 is included in the X-ray apparatus 100 of FIG. 1, the medical image capturing unit corresponds to the medical image capturing unit 115 of FIG. 1 and may include the high voltage generator 121, the X-ray irradiation unit 120, and the detector 130. Also, the first control unit 310 controls the medical image capturing unit so as to control an irradiation timing of the X-ray, an intensity of the X-ray, and an irradiation region of the X-ray.

When a first software component 340 is in an active state, the first control unit 310 may control capturing of the object based on the first software component 340. The first software component 340 may be in at least one of an active state, a failure state, and a standby state. When the first software component 340 is in the active state, it may be understood that the first software component 340 normally operates. When the first software component 340 is in the failure state, it may be understood that an error such as a halt of first software component 340 occurs in the first software component 340. When the first software component 340 is in the standby state, it may be understood that the first software component 340 is loaded in a memory, but does not occupy an execution context of a CPU.

In detail, the active state may mean a state in which the first software component 340 operates and performs a certain task. For example, when the first software component 340 includes a program configured to control capturing of a fluoroscopy image, if the first software component 340 is in the active state, the first software component 340 controls the capturing of the fluoroscopy image, and X-ray photographing for acquiring the fluoroscopy image may be performed. Also, the standby state may mean a state in which a particular task is not currently performed, but may be changed into the active state according to an execution command. In detail, the first control unit 310 executes a first software application 330 in order to set the first software component 340 to be in the active state. Alternatively, the first control unit 310 separately executes the first software component 340 and may set the first software component 340 to be in the active state. Alternatively, the first control unit 310 may set the first software component 340, which is in the standby state, is loaded in the memory, but does not occupy the execution context of the CPU, to be in the active state. As described above, the active state of the first software component 340 may mean that the first control unit 310 sets the first software component 340 to perform its functions.

The first control unit 310 may periodically monitor a state of the first software component 340 included in the first software application 330.

As described above, the first software application 330 may be designed based on a software component. Therefore, the first software application 330 may include a plurality of software components 331, 332, 333, 334, and 340, and the first software component 340 may be any one of the plurality of software components 331, 332, 333, 334, and 340 included in the first software application 330.

For example, the first software application 330 of the X-ray imaging apparatus for angiography or a surgical operation may include a software component such as a software component configured to control fluoroscopy photographing, a software component configured to measure or manage vital signs of an object, for example, respiration, pulses, a body temperature, electrocardiogram, etc., and a software component configured to set an X-ray photographing mode such as a digital subtraction angiography (DSA), and a roadmap.

The first software component 340 may control the fluoroscopy photographing or may acquire a fluoroscopy image. As described above, when a fluoroscopy function used to monitor an invasive operation such as the angiography or a surgical operation, which is being performed, has an unexpected fault, a patient who undergoes the invasive operation may be fatally affected. Therefore, the fluoroscopy function which is crucial for a smooth performance of the operation and the safety of the patient in the above-described environment may be used as a software component of an X-ray apparatus, and a fault-tolerant system for the fluoroscopy function may be designed.

The first control unit 310 may periodically monitor the state of the first software component 340 in order to check whether the first software component 340 is in the active state or normally operates. For example, the first control unit 310 monitors the state of the first software component 340 once per second and may check whether the first software component 340 normally operates or has any fault such as a halt of the first software component 340.

When the first software component 340 is in the failure state, the first control unit 310 may set any one of the second software components 350, 351 and 352 which are the same as the first software component 340 to be in an active state and may control the capturing of the medical images to continue being performed.

In detail, the medical imaging apparatus 300 may include at least one of the second software components 350, 351 and 352 which have the same structure and functions as the first software component 340 in order to establish the fault-tolerant system for the first software component 340.

When the first control unit 310 detects that the first software component 340 is in the failure state while the state of the first software component 340 is being periodically monitored, the first control unit 310 may set any one of the second software components 350, 351 and 352 to be in the active state. Also, the first control unit 310 may set the first software component 340 to be in a non-active state. That is, the first control unit 310 may stop the operation of the first software component 340 to prevent a conflict between the first software component 340 and the at least one second software component 350, 351 and 352 which is set to be in the active state.

In detail, when the first software component 340 is in the failure state, the first control unit 310 may execute any one of the second software components 350, 351 and 352 and may set the executed one of the second software components 350, 351 and 352 to be in the active state. Alternatively, the first control unit 310 is loaded in the memory and may set any one of the second software components 350, 351 and 352, which is not executed and is in the standby state, to be in the active state.

The medical imaging apparatus 300 may perform failover with respect to its function via the second software components 350, 351 and 352, even though the first software component 340 has a fault. In addition, the medical imaging apparatus 300 may effectively perform failover with respect to a predetermined function requiring continuity and stability instead of performing failover with respect to the entire system.

For example, the medical imaging apparatus 300 may design the fluoroscopy function to be the first software component 340. Thus, although the fluoroscopy function is unexpectedly discontinued while an invasive operation such as angiography or a surgical operation is being performed, the medical imaging apparatus 300 may activate any one of the second software components 350, 351 and 352 and may perform failover with respect to the fluoroscopy function.

FIG. 4 is a view for explaining operations of a medical imaging apparatus 400 according to an exemplary embodiment.

FIG. 4 illustrates a structure of the medical imaging apparatus 400 which may perform failover with respect to a fluoroscopy function. That is, the medical imaging apparatus 400 may be included in an X-ray apparatus. In detail, the medical imaging apparatus 400 may be included in the workstation 110 of FIG. 1 or the workstation (not shown) of the C-arm X-ray apparatus of FIG. 2.

Also, the medical imaging apparatus 400 may correspond to the medical imaging apparatus 300 of FIG. 3. In detail, a first control unit 410, a software application 430, a first software component 440, and second software components 450, 451 and 452 may respectively correspond to the first control unit 310, the software application 330, the first software component 340, and the second software components 350, 351 and 352 of FIG. 3. Thus, the descriptions which have been already provided with reference to FIG. 3 will be omitted.

The software application 430 includes software components 431, 432, 433, 434 and 440, and the software components 431, 432, 433, 434 and 440 may independently operate. Also, the software components 431, 432, 433, 434 and 440 may be separable from the software application 430, and the first software component 440 may be any one of the software components 431, 432, 433, 434 and 440.

The first software component 440 may control the fluoroscopy photographing or may acquire a fluoroscopy image in the X-ray apparatus 100. The software component 433 may measure or manage vital signs of an object such as respiration, pulses, a body temperature, and electrocardiogram. Moreover, the software component 434 may set an X-ray photographing mode such as DSA and a roadmap.

Furthermore, the software application 430 may include the software components 431 and 432 necessary to control the X-ray apparatus 100.

As described above, since the software application 430 may operate based on the software components 431, 432, 433, 434 and 440, each of the software components 431, 432, 433, 434 and 440 may be separable from functions of the software application 430 or other software components.

For example, the first software component 440 may be separable from the software application 430. In detail, the first control unit 410 separates the first software component 440 from the software application 430 to independently operate the first software component 440 and may display a fluoroscopy image 441 which is acquired during the fluoroscopy photographing on a display screen 420b. Also, an algorithm or code corresponding to the first software component 440 may be easily separable from an algorithm or code corresponding to the software application 430. The first software component 440 may be replaced with software components having the same functions as the second software components 450, 451 and 452 and may be reused in another software application. However, as described above, the first software component 440 may be closely related to the software components 431, 432, 433 and 434 in consideration of an entire software application 430.

FIG. 4 illustrates operations of the medical imaging apparatus 400.

FIG. 4 illustrates a display screen 420b of the medical imaging apparatus 400 when the first software component 440 is in the active state. In detail, the display screen 420b is an execution screen of a software application. The execution screen of the software application may include an execution screen 441 of the first software component 440 corresponding to the fluoroscopy function, an execution screen 470 of the software component 433 corresponding to a function for measuring or managing vital signs of the object, and an execution screen 480 of the software component 434 corresponding to a function for setting an X-ray photographing mode.

FIG. 4 illustrates a display screen 420c of the medical imaging apparatus 400 before the second software component 450 is set to be in the active state, after the first software component 440 is in the failure state. In detail, when the first software component 440 has a fault such as display discontinuation of the fluoroscopy image, an error message 490 may be displayed on the display screen 420c. For example, the error message 490 may include a message saying "Exception Occurred" and indicating the occurrence of an unexpected exceptional situation. Also, even when an entire software application has a fault, if the first software component 440 is in the failure state, the error message 490 may be displayed on the display screen 420c.

In the case of the fluoroscopy image, when a function for monitoring an invasive operation such as angiography or a surgical operation has an unexpected fault, a patient or object may be fatally affected.

Referring to FIG. 4, after the first software component 440 is in the failure state, the second component 450 is set to be in the active state to continue to capture a fluoroscopy image, and a fluoroscopy image 495 acquired due to the continuation of the fluoroscopy photographing may be displayed on a display screen 420d of the medical imaging apparatus 400.

In detail, when the first software component 440 is in the failure state, the first control unit 410 may set any one of the second software components 450, 451 and 452, for example, the second software component 450, to be in the active state.

Therefore, unlike the display screen 420b, the display screen 420d only displays the fluoroscopy image 495 thereon because the second software component 450 corresponding to the fluoroscopy function is set to be in the active state.

Therefore, the medical imaging apparatus 400 may provide a rather safe operation environment by establishing the fault-tolerant system for the fluoroscopy image.

FIG. 5 is a block diagram of a structure of a medical imaging apparatus 500 according to another exemplary embodiment.

In comparison with the medical imaging apparatus 300 of FIG. 3, the medical imaging apparatus 500 may further include at least one of a first memory 560 including at least one second software component 541, a display 570, and a communication unit 580.

Also, the first control unit 510 may correspond to the first control unit 310 of FIG. 3. In particular, a first software application 530, a first software component 531, and the second software component 541 of FIG. 5 may respectively correspond to the first software application 330, the first software component 340, and the second software component 350 of FIG. 3. Therefore, the descriptions which have been already provided with reference to FIG. 3 will be omitted.

When the first software component 531 is in the active state, the first control unit 510 loads at least one second software component 541, 542 and 543 in the first memory 560 and may set the at least one second software component 541, 542 and 543 to be in the standby state.

In particular, the first control unit 510 may set the at least one second software component 541, 542 and 543 to be loaded in the first memory 560 but not to occupy the execution context (CPU). Thus, the medical imaging apparatus 500 may quickly and effectively perform failover with respect to a function corresponding to the first software component 531 when the first software component 531 has a fault.

Also, the first memory 560 may store information regarding the medical imaging apparatus 500. For example, the first memory 560 may store at least one of current states of the first software application 530, the first software component 531, and the second software component 541, input/output values, and control parameters. In addition, the first memory 560 may store medical images acquired from the object.

When the first software component 531 is in the failure state, the first control unit 510 sets any one of the second software components 541, 542 and 543, which have been in the standby state, to be in an active state and may continue to capture the medical images. That is, the medical imaging apparatus 500 may perform failover with respect to its functions via the second software components 350, 351 and 352 even though the first software component 340 has a fault.

The first control unit 510 may periodically acquire at least one piece of state information included in the first software component 531 and may set any one of the second software components 541, 542 and 543, which have been in the standby state, to be in the active state based on the at least one acquired piece of the state information when the first software component 531 is in the failure state.

The state information may include control parameters, user setting information, photographing information of the medical imaging apparatus, or the like. That is, the state information may include all pieces of information necessary to operate the second software component 541 in the same situations and under the same conditions as the situations and conditions set right before the first software component 531 stops operating. Therefore, the first control unit 510 may set the second software component 541 to have the same situations and the same conditions as those set right before the first software component 531 enters the failure state. The medical imaging apparatus 500 may maintain the continuity between the medical images, which are captured right before the first software component 531 enters the failure state, and the medical images, which are captured right after the second software component 541 is set to be in the active state.

Also, the first control unit 510 may set the second software components 541, 542 and 543, which has been in the active state, to be in the standby state when the first software component 531 which has been in the failure state is set to be in the active state again. That is, when the function of first software component 531 is restored, the second software component 541 is no longer in the active state.

The first control unit 510 may include software applications 530, 540, 590 and 591. For example, the first control unit 510 may include the first software application 530 used to control the medical imaging apparatus 500, the second software application 540 used to perform failover with respect to the function of first software component 531, and other software applications 590 and 591.

The second software application 540 may further include a failover manager software component 544 other than the second software component 541. The failover manager software component 544 periodically monitors the state of the first software component 531 and may perform failover with respect to the function of first software component 531 by setting any one of the second software components 541, 542 and 543 to be in the active state when the first software component 531 is in the failure state. Operations of the failover manager software component 544 will be described in detail with reference to FIG. 6.

The display 570 may display an output screen of the first control unit 510 which is configured to control the medical imaging apparatus 500. For example, like the display screen 420*b*, the display screen 420*c*, and the display screen 420*d* of FIG. 4D, the display 570 may display an execution screen of a software application. In detail, the display 570 may display a UI, and information necessary for the user to manipulate the medical imaging apparatus 500, for example, user information, object information, or the like.

The communication unit 580 may receive/transmit internal and external data of the medical imaging apparatus 500. The communication unit 580 may correspond to the communication unit (not shown) of the X-ray apparatus 100 of FIG. 1. Therefore, the descriptions which have been already provided with reference to FIG. 1 will be omitted.

FIGS. 6A and 6B respectively are a flowchart and a block diagram for explaining operations of a medical imaging apparatus according to another exemplary embodiment. In detail, FIG. 6A illustrates that a failover manager software component 600 performs failover with respect to functions of a first software component 610 via a second software component 620.

In operation S600, the failover manager software component 600 (hereinafter, referred to as the "failover manager") may request a current state of the first software component 610. When the first software component 610 is in the active state, that is, when the first software component 610 normally operates, the failover manager 600 may continuously request the current state of the first software component 610. For example, the failover manager 600 may perform operation S600 once per second. That is, the failover manager 600 may periodically monitor the state of the first software component 610.

In operation S610, when the first software component 610 is not in the active state, for example, when the first software component 610 is in a failure state such as when a functional error occurs, the failover manager 600 may set any one of the second software components 620 to be in the active state in operation S620. That is, the failover manager 600 may perform failover with respect to a function corresponding to the first software component 610 by using the second software components 620.

In operation S630, if the first software component 610 normally operates again, the failover manager 600 may continuously request the first software component 610 to transmit the current state of the first software component 610 in order to stop the active state of the second software component 620.

In operation S640, when the first software component 610 is in the active state, that is, when the first software component 610 normally operates again, the failover manager 600 may set the second software components 620, which has been in the active state, to be in the standby state in operation S650.

FIG. 6B illustrates connections of the failover manager 600, the first software component 610, and the second software components 620. The failover manager 600 periodically monitors the state of the first software component 610 and may set a state of the second software components 620 based on the state of the first software component 610.

FIG. 7 illustrates operations of a medical imaging apparatus according to another exemplary embodiment. In detail, FIG. 7 illustrates operations of the medical imaging apparatus 500 of FIG. 5 which may perform failover with respect to fluoroscopy functions. Also, unlike FIG. 4, FIG. 7 illustrates a display screen on which a second software component is set to be in the standby state.

FIG. 7 illustrates a display screen of the medical imaging apparatus 500 of FIG. 5 when a first software component is in an active state. In comparison with the display screen 420*b* of FIG. 4, an indicator 700 indicating the second software component, which is set to be in the standby state, is further included in the display screen of FIG. 7. For example, the second software component, which is set to be in the standby state, may be displayed as a bar-type window 700. Alternatively, when the first software component is in the active state, the indicator 700 indicating the second software component, which is set to be in the standby state, may not be displayed.

Also, an execution screen 741 of the first software component which corresponds to the fluoroscopy function, an execution screen 770 of another software component which corresponds to a function for measuring or managing vital signs of an object, and an execution screen 780 of the other software component which corresponds to a function for setting an X-ray photographing mode may each correspond to the execution screens 441, 470 and 480 of FIG. 4. Therefore, the descriptions which have been provided with reference to FIG. 4 will be omitted.

FIG. 7 illustrates a display screen of the medical imaging apparatus 500 which is shown before the second software component enters the active state and after the first software component enters the failure state. In detail, since the second software component is still in the standby state, the second software component may be displayed as the bar-type window 710. An error message 790 notifying the failure state of the first software component may correspond to the error message 490 of FIG. 4. Therefore, the descriptions which have been already provided with reference to FIG. 4 will be omitted.

FIG. 7 illustrates a display screen of the medical imaging apparatus 500, on which the second software component is set to be in the active state, after the first software component enters the failure state. In detail, a fluoroscopy image 751 may be displayed on the display screen via the second software component which is in the active state. Also, the fluoroscopy image 751 which is created in accordance with the activation of the second software component may include the indicator 710 indicating that the second software component is in the active state.

When the first software component is in the failure state, the medical imaging apparatus 500 sets the second software component to be in the active state, and thus, it may be possible to quickly and effectively perform failover with respect to a function which corresponds to the first software component.

In addition, the first control unit 510 may periodically acquire at least one of a fluoroscopy photographing condition included in state information of the first software component 531, user setting information and a current state of the software application. The current state of the software application may mean a current execution operation when the software application includes a plurality of execution operations.

Also, when the first software component is in the failure state, the first control unit 510 sets any one of the second software components, which have been in the standby state, to be in the active state based on acquired state information and may control the capturing of the medical images to continue being performed. The medical imaging apparatus 500 may set the second software component 541 to be in the active state based on the state information acquired from the first software component 531 so that the second software component 541 may have the same situations and conditions as the first software component 531, the situations and conditions set right before the first software component 531 enters the failure state.

FIG. 8 is a block diagram of a structure of a medical imaging apparatus 800 according to another exemplary embodiment.

The medical imaging apparatus 800 may establish a fault-tolerant system based on a software component like the medical imaging apparatus 300 of FIG. 3 or the medical imaging apparatus 500 of FIG. 5, and may also establish a fault-tolerant system which is more stable by replicating a hardware component. That is, the medical imaging apparatus 800 may further include a second control unit 825 in preparation for an abnormal operation of the first control unit 820, for example, discontinuance of power supply to the hardware component of the first control unit 820, the unexpected occurrence of an error in an entire system of the first control unit 820, or the like.

The first control unit 820 may be in at least one of the active state and the failure state. When the first control unit 820 is in the active state, it may be understood that the first control unit 820 normally operates. When the first control unit 820 is in the failure state, it may be understood that an error such as the halt of the first control unit 820 occurs. Also, if the power supply to the first control unit 820 is unexpectedly discontinued, the first control unit 820 may be in the failure state. Also, if the first software component 840 and all of the second software components abnormally operate, the first control unit 820 may be in the failure state.

The first control unit 820, a software application 830, a first software component 840, a second software component 850, a first memory 860, a first display 870, and a first communication unit 880 of the medical imaging apparatus 800 of FIG. 8 may respectively correspond to the first control unit 520, the software application 530, the first software component 531, the second software component 541, the memory 560, the display 570, and the communication unit 580 of the medical imaging apparatus 500 of FIG. 5. Therefore, the descriptions which have been provided with reference to FIG. 5 will be omitted.

In comparison with the medical imaging apparatus 500 of FIG. 5, the medical imaging apparatus 800 of FIG. 8 may further include at least one of a second memory 885 including at least one third software component 845 which is the same as the first software component, and the second control unit 825.

When the first control unit 820 is in the active state, the first control unit 820 and the second control unit 825 may be used together in the medical imaging apparatus 800 for load-balancing. That is, the second control unit 825 may perform the same function as the first control unit 820. Alternatively, when the first control unit 820 is in the active state, the second control unit 825 may be used for a different purpose and usage from the first control unit 820. For example, the first control unit 820 may be used to control fluoroscopy photographing or acquire a fluoroscopy image, and when the first control unit 820 is in the active state, the second control unit 825 may be used to acquire a DSA image, a roadmap image, a cone beam CT image, or the like.

When the first control unit 820 is in the active state, the second control unit 825 loads the at least one third software component 845 which is the same as the first software component 840 in the second memory 885 and may set the at least one third software component 845 to be in the standby state. That is, when the first control unit 820 is in the failure state, the second control unit 825 may load the at least one third software component 845 in the second memory 885 in order to continuously, quickly and effectively capture medical images.

Also, the second memory 885 may store information regarding the medical imaging apparatus 800. For example, the second memory 885 may store at least one of a current state of the at least one third software component 845, input/output values, and a control parameter. Moreover, the second memory 885 may store the medical images acquired from the object. The second memory 885 may be a hardware component independent from the first memory 860. Alternatively, the second memory 885 and first memory 860 may be included in a single memory. That is, the second memory 885 may be a hardware device connected to the first memory 860.

When the first control unit 820 is in the failure state, the second control unit 825 sets any one of the at least one third software component 845 which is the same as the first software component 840 to be in the active state and may control the capturing of the medical images to continue being performed. That is, when the first control unit 820 is in the failure state, the second control unit 825 effectively performs failover with respect to predetermined functions requiring continuity and stability by executing the at least one third software component 845 and may continue to capture the medical images.

The second control unit 825 may periodically acquire at least one piece of state information included in the first software component 840 or in the second software component 850. In addition, when the first control unit 820 is in the failure state, the second control unit 825 sets any one of the at least one third software component 845, which has been in the standby state, to be in an active state based on the at least one acquired piece of the state information and may control the capturing of the medical images to continue being performed.

The state information may include a control parameter of the first software component 840 or the second software component 850, the user setting information, and photographing information of the medical imaging apparatus 800. That is, the state information may include all pieces of information necessary to operate the at least one third software component 845 in the same situations and under the same conditions as the first software component 840 or the second software component 850, the situations and conditions set right before the first software component 840 or the second software component 850 stops operating. Therefore, the second control unit 825 may set the at least one third software component 845 to have the same situations and under the same conditions as the first software component 840 or the second software component 850 as the situations and conditions set right before the first software component 840 or the second software component 850 enters the failure state. As a result, the medical imaging apparatus 800 may maintain the continuity of the capturing of the medical images.

In particular, when the first software component 840 is in the active state, the second control unit 825 may periodically acquire the state information of the first software component 840. When the first software component 840 is in the failure state, for example, when an error occurs in an entire system of the first control unit 820 including the first software component 840 and the second software component 850 or the power supply to the first control unit 820 is discontinued, the second control unit 825 may set the at least one third software component 845 to be in the active state based on the state information acquired from the first software component 840.

Also, when the second software component 850 is in the active state because the first software component 840 is in the failure state, the second control unit 825 may periodically acquire the state information of the second software component 850. Then, when the second software component 850 is in the failure state, or when the first control unit 820 is in the failure state, for example, the discontinuation of the power supply to the first control unit 820, the second control unit 825 may set the at least one third software component 845 to be in the active state based on the state information acquired from the second software component 850.

The medical imaging apparatus 800 may maintain the continuity between the medical images, which are captured right before the first control unit 820 enters the failure state, and the medical images, which are captured right after the at least one third software component 845 is set to be in the active state.

The medical imaging apparatus 800 may further include at least one of a second display 875 and a second communication unit 865.

The second display 875 may display an output screen of the second control unit 825 which is configured to control the medical imaging apparatus 800. For example, the second display 875 may display an execution screen of the second software component 850. In detail, the second display 875 may display a user interface (UI) and information such as user information or object information which is necessary for the user to manipulate the medical imaging apparatus 800.

The second communication unit 865 may receive/transmit internal and external data of the medical imaging apparatus 800. Also, the communication unit 580 of FIG. 5 may correspond to a communication unit (not shown) of the X-ray apparatus of FIG. 1. Therefore, the descriptions which have been already provided with reference to FIG. 1 will be omitted.

The second control unit 825 may periodically monitor the state of the first control unit 820. In detail, the second communication unit 865 communicates with the first communication unit 880 via a network 890 and may determine whether the first control unit 820 is in the active state or the failure state. The network 890 may be a wired or wireless network, but is not limited thereto.

The medical imaging apparatus 800 may include a first workstation 810 which includes the first control unit 820 and the first memory 860 and a second workstation 815 which includes the second control unit 825 and the second memory 885. In addition, the first workstation 810 and the second workstation 815 may be independent hardware devices.

The first workstation 810 and the second workstation 815 may separately receive power. Thus, although the power is not supplied to the first workstation 810 at an unexpected point in time, the medical images may continue to be captured via the second workstation 815. Also, if the first workstation 810 and the second workstation 815 receive power from the same source, the medical images may continue to be captured via the second workstation 815 even though a mechanical error only occurs in the first workstation 810.

As described above, when the first control unit 820 is in the active state, the first control unit 820 included in the first workstation 810 and the second control unit 825 included in the second workstation 815 may perform different functions. For example, the first workstation 810 corresponds to an acquisition workstation (AWS), and the first control unit 820 may control the medical imaging apparatus 800 or may display date acquired from the medical imaging apparatus 800. In addition, the second workstation 815 corresponds to a visualization workstation (VWS), and when the first control unit 820 is in the active state, the second control unit 825 may reconfigure the data acquired from the medical imaging apparatus 800 and may display a reconfiguration result. Alternatively, the first control unit 820 of the first workstation 810 generates real-time data, for example, the fluoroscopy image, and the second control unit 825 of the second workstation 815 may generate non-real time data, for example, a cone-beam CT image.

FIG. 9 illustrates operations of a medical imaging apparatus according to another exemplary embodiment.

In detail, FIG. 9 illustrates operations of the medical imaging apparatus 800 of FIG. 8 which may perform failover with respect to a fluoroscopy function. That is, the medical imaging apparatus 800 of FIG. 8 may be included in an X-ray apparatus. In detail, the medical imaging apparatus 800 of FIG. 8 may be included in the workstation 110 of FIG. 1 or a workstation (not shown) of the C-arm X-ray apparatus of FIG. 2. As illustrated in FIGS. 4 to 7, the first software component 840 may control the capturing of a fluoroscopy image or may acquire a fluoroscopy image.

FIG. 9 illustrates a display screen 901 (hereinafter, referred to as the "first display screen") of the first display 870 and a display screen 902 (hereinafter, referred to as the "second display screen") of the second display 875 when the first control unit 820 is in the active state.

The first display screen 901 is output according to control of the first control unit 820 and may correspond to the display screen 420*b* of FIG. 4. That is, the first display screen 901 is an execution screen of a software application. In detail, the first display screen 901 may include an execution screen 900 of the first software component 840 configured to perform a fluoroscopy function.

The second display screen 902 may be output according to control of the second control unit 825. In detail, the second control unit 825 performs different functions from the first control unit 820, and the second display screen 902 may include non-real time information 910 with regard to the object. Also, the second display screen 902 may include a bar-type window 920 indicating the at least one third software component 845 which is set to be in the standby state.

FIG. 9 illustrates the first display screen 901 and the second display screen 902 when the first control unit 820 is in the failure state.

In detail, like a case where the capturing of the fluoroscopy image is terminated by the first control unit 820, when the first control unit 820 is in the failure state, a blue screen 930 may be shown on the first display screen 901. In this case, the second control unit 825 is the same as the first software component and may set any one of the at least one third software component 845, which is set to be in the standby state, to be in the active state. As a result, the second display screen 902 may include an execution screen 950 of the at least one third software component 845 which performs a fluoroscopy function. Also, a screen 950 may include an indicator 940 indicating that the at least one third software component 845 is in the active state.

FIG. 10 is a flowchart of a method of capturing a medical image by using a medical imaging apparatus, according to an exemplary embodiment. In detail, referring to FIG. 10, although a first software component is in a failure state, a second software component may be set to be in an active state, and thus, capturing of the medical image may continue. The method may be performed by the medical imaging apparatuses 300 and 500 described with reference to FIGS. 3 and 5. In addition, each operation of the method includes the same technical idea as that of the medical imaging apparatuses 300 and 500. Therefore, the descriptions which have been already provided with reference to FIGS. 3 and 9 will be omitted.

In operation S1010, the first control units 310 and 510 of the medical imaging apparatuses 300 and 500 may control capturing of an image of an object based on the first software component when the first software component is in the active state.

In operation S1020, the first control units 310 and 510 of the medical imaging apparatuses 300 and 500 may periodically monitor a state of the first software component included in a software application.

In operation S1030, the first control units 310 and 510 of the medical imaging apparatuses 300 and 500 may set any one of at least one second software component which is the same as the first software component to be in an active state and may continue to capture the image of the object when the first software component is in a failure state.

As described above, the medical imaging apparatus according to the one or more exemplary embodiments of the inventive concept may perform failover with respect to predetermined functions and may continue to capture medical images even though the predetermined functions requiring continuity or stability have faults.

The above-described exemplary embodiments of the inventive concept may be written as computer programs and may be implemented in general-use digital computers that execute the programs using a non-transitory computer-readable recording medium.

Examples of the non-transitory computer-readable recording medium include magnetic storage media (e.g., ROM, floppy disks, hard disks, etc.), optical recording media (e.g., CD-ROMs, or DVDs), etc), and transmission media such as Internet transmission media.

While the inventive concept has been particularly shown and described with reference to exemplary embodiments thereof, it will be understood by those of ordinary skill in the art that various changes in form and details may be made therein without departing from the spirit and scope of the inventive concept as defined by the following claims.

The invention claimed is:

1. A medical imaging apparatus comprising:
a medical image capturing unit configured to capture medical images of an object; and
a first control unit configured to:
control the medical image capturing unit to capture an image of the object based on a first software component when the first software component is in an active state;
periodically monitor a state of the first software component included in a software application; and
set a second software component, which is configured to perform a same function as the first software component, to be in an active state when the first software component is in a failure state so as to control the medical image capturing unit to continue capturing of the image of the object.

2. The medical imaging apparatus of claim 1, wherein the first software component is separable from the software application.

3. The medical imaging apparatus of claim 1, wherein the software application comprises a plurality of software components,
the plurality of software components independently operate and are separable from the software application, and
the first software component is any one of the plurality of software components.

4. The medical imaging apparatus of claim 1, further comprising a first memory configured to store the second software component,
wherein the first control unit is configured to:
set the second software component stored in the first memory to be in a standby state; and
set the second software component, which is set to be in the standby state, to be in the active state when the first software component is in the failure state so as to control the medical image capturing unit to continue capturing of the image of the object.

5. The medical imaging apparatus of claim 4, wherein the first control unit is configured to:
periodically acquire state information included in the first software component; and
set the second software component, which is set to be in the standby state, to be in the active state based on the state information when the first software component is in the failure state.

6. The medical imaging apparatus of claim 4, wherein the first control unit is configured to set the second software component, which is set to be in the active state, to be in a standby state when the first software component is set to be in the active state.

7. The medical imaging apparatus of claim 1, wherein the first software component is configured to control capturing of a fluoroscopy image or control acquiring of a fluoroscopy image.

8. The medical imaging apparatus of claim 5, wherein the first software component is configured to control capturing of a fluoroscopy image or control acquiring of a fluoroscopy image, and
the state information comprises at least one of a condition for capturing the fluoroscopy image, user setting information, or a current state of the software application.

9. The medical imaging apparatus of claim 4, further comprising:
a second memory configured to store a third software component which is configured to perform a same function as the first software component; and
a second control unit configured to:
set the third software component stored in the second memory to be in a standby state when the first control unit is in an active state; and
set the third software component, which is set to be in the standby state, to be in an active state when the first control unit is in a failure state so as to control the medical image capturing unit to continue capturing of the image of the object.

10. The medical imaging apparatus of claim 9, wherein the second control unit is configured to:
periodically acquire state information included in the first software component or in the second software component; and
set the third software component, which is set to be in the standby state, to be in the active state based on the state information when the first control unit is in the failure state so as to control the medical image capturing unit to continue capturing of the image of the object.

11. The medical imaging apparatus of claim 9 further comprising:
a first workstation comprising the first control unit and the first memory; and
a second workstation comprising the second control unit and the second memory,
wherein the first workstation and the second workstation are hardware devices which are independent from each other.

12. A method of capturing a medical image by using a medical imaging apparatus, the method comprising:
capturing medical images of an object by using a medical image capturing unit;
controlling the medical image capturing unit to capture an image of the object based on a first software component when the first software component is in an active state;
periodically monitoring a state of the first software component included in a software application; and
controlling the medical image capturing unit to continue capturing of the image of the object by setting a second software component which is configured to perform a same function as the first software component to be in an active state when the first software component is in a failure state.

13. The method of claim 12, further comprising:
loading the second software component in a first memory; and
setting the second software component loaded in the first memory to be in a standby state when the first software component is in the active state,
wherein controlling the medical image capturing unit to continue capturing of the image of the object comprises setting the second software component, which is set to be in the standby state, to be in an active state when the first software component is in the failure state so as to control the medical image capturing unit to continue capturing of the image of the object.

14. The method of claim 12, further comprising:
periodically acquiring state information included in the first software component,
wherein the controlling the medical image capturing unit to continue capturing of the image of the object comprises setting the second software component, which is set to be in a standby state, to be in the active state based on the state information when the first software component is in the failure state.

15. A non-transitory computer-readable recording medium having embodied thereon a computer program for executing the method of claim 12.

* * * * *